United States Patent [19]
Ono

[11] Patent Number: 5,267,858
[45] Date of Patent: Dec. 7, 1993

[54] AVERAGE MOVEMENT ARTICULATOR CAPABLE OF BEING SET FOR FREE MOVEMENT

[76] Inventor: Yasunori Ono, 3-1, Daimon 1-chome, Kokurakita-ku, Kitakyushu-shi, Fukuoka, Japan

[21] Appl. No.: 28,476

[22] Filed: Mar. 9, 1993

[30] Foreign Application Priority Data

Oct. 15, 1992 [JP] Japan .................. 4-277500
Oct. 21, 1992 [JP] Japan .................. 4-283143

[51] Int. Cl.⁵ .............................................. A61C 11/00
[52] U.S. Cl. ................................................ 433/58
[58] Field of Search ................ 433/54, 57, 58, 60, 433/61, 62, 65

[56] References Cited

U.S. PATENT DOCUMENTS

| | | | |
|---|---|---|---|
| 682,668 | 9/1901 | Bruce | 433/62 |
| 1,517,922 | 12/1924 | Stanley | 433/57 |
| 2,445,639 | 7/1948 | Sandhofer | 433/58 |
| 2,670,538 | 3/1954 | Thompson | 433/58 |
| 4,175,325 | 11/1979 | Beckwith | 433/60 |

*Primary Examiner*—Cary E. O'Connor
*Attorney, Agent, or Firm*—Jordan and Hamburg

[57] ABSTRACT

The present invention provides an average movement articulator capable of being set for free movement, having lower frame, and an upper frame capable of being moved longitudinally, vertically and laterally and being turned about a longitudinal axis relative to the lower frame and of being turned about a lateral axis for free movement in analyzing occlusion, restoring decayed teeth and making crown bridges. The articulator substantially comprises a) a lower frame holding a lower working cast on its upper surface; b) an upper frame disposed above the lower frame and holding an upper working cast on its lower surface; c) a pair of support struts standing upright at the opposite ends, respectively, of the rear end of the lower frame; d) a transverse member supported on the respective upper ends of the support struts so as to be swingable about a lateral axis and longitudinally movable; and e) resilient connecting members resiliently connecting the rear end of the upper frame to the transverse member so that the upper frame is able to move vertically, laterally and longitudinally and to turn relative to the transverse member; wherein the upper frame is able to move longitudinally, vertically and laterally and to turn about a longitudinal axis relative to the lower frame.

3 Claims, 7 Drawing Sheets

AVERAGE MOVEMENT ARTICULATOR CAPABLE OF BEING SET FOR FREE MOVEMENT

BACKGROUND OF THE INVENTION

The present invention relates to an average movement articulator capable of being set for free movement, wherein an upper frame is moved longitudinally, vertically, laterally, or rotatably relative to a lower frame or the upper frame is pivoted vertically in analyzing occlusion, restoring decayed teeth and making crown bridges.

When restoring decayed tooth or making a crown bridge or a denture, working casts of the patient's upper and lower jaws are formed, the working casts are mounted on an articulator, such as a simplified, small-sized articulator, an average movement articulator or an adjustable articulator, the working casts are occluded or eccentrically moved, the movement of the patient's jaws is measured, the articulator is adjusted on the basis of the results of trial occlusion and measurement and the working casts are mounted on the adjusted articulator for the analysis of occlusion, the restoration of a decayed tooth, making a crown bridge or a denture, and the adjustment of a crown bridge or a denture.

Such an articulator is constructed by pivotally mounting an upper frame for supporting an upper working cast on a lower frame for supporting a lower working cast. The upper frame is opened or closed hingedly on the pivoted shaft for center occlusion and backward condyle path movement to make the upper and lower working casts simulate the movement of the patient's jaws.

The conventional articulators, however, have the following disadvantages.

The simplified, small-size articulator is able to hold small working casts of only two to four teeth and incapable of accurately simulating motions of jaws, because the simplified, small-size articulator has an inclination of condyle path allowing only slight motions of jaws and is capable of vertical opening and closing motion.

The average movement articulator is capable of hinged opening and closing motion and the condyle path movement is fixed to an average movement. Therefore, the average movement articulator is able to move only within a limited angular range and unable to deal with various cases.

The adjustable articulator is provided with a plurality of adjusting mechanisms to enable the adjustable articulator to simulate the movement of human jaws and has the same size as the human maxillary structure. Therefore, the adjustable articulator has a complicated construction, is very large and heavy and is very cumbersome to use.

A free movement articulator has an upper frame, a lower frame and springs interconnecting the upper and lower frames. However, the free movement articulator is unable to simulate the movement of the jaws and unable to function accurately for the restoration and adjustment of a decayed tooth since the frame is twisted or a play exists on the pivoting shaft.

Accordingly, it is an object of the present invention to provide an average movement articulator capable of being set for free movement and of solving the foregoing problems in the prior art.

SUMMARY OF THE INVENTION

The present invention provides an average movement articulator capable of being set for free movement, comprising a) a lower frame holding a lower working cast on its upper surface, b) an upper frame disposed above the lower frame and holding an upper working cast on its lower surface, c) a pair of support struts standing upright at the opposite ends, respectively, of the rear end of the lower frame, d) a transverse member supported on the respective upper ends of the support struts so as to be swingable about a lateral axis and longitudinally movable; and e) resilient connecting members resiliently connecting the rear end of the upper frame to the transverse member so that the upper frame is able to move vertically, laterally and longitudinally and to turn relative to the transverse member; wherein the upper frame is able to move longitudinally, vertically and laterally and to turn about a longitudinal axis relative to the lower frame.

In the above average movement articulator, a pair of inclined support arms extend obliquely upward toward the rear from the upper ends of the support struts, respectively, the transverse member is movable along upper surfaces of the inclined supports arms, the transverse member is pressed resiliently against the inclined support arms by presser rods, the upper frame is able to move longitudinally together with the transverse member along the inclined surfaces of the inclined support arms, and the upper frame is able to swing about a lateral axis.

Furthermore, in the average movement articulator, the upper frame is provided with fastening means for fastening together the upper frame and the transverse member.

When the fastening means, such as spring fastening screws, is unfastened, because the upper frame and the transverse member are joined together by the resilient connecting members, such as springs, the joint of the average movement articulator is able to move like joint of the conventional articulator when the upper frame moves for free movement in vertical directions, longitudinal directions and lateral directions and for swing motion. Thus, different from the totally free movement of the conventional free movement articulator, the free movement of the average movement articulator of the present invention is regulated or guided by the averaging movement of the joint. Namely, the average movement of the joint cooperates with the free movement to enhance the reliability of eccentric movement during the free movement, and, consequently, the average movement articulator is able to move according to the movement of the patient's jaws. Thus, the average movement articulator is capable of operating for centric occlusion and eccentric movement according to the abraded surface of the patient's teeth, the height of the cusps of the patient's teeth, the positions of the patient's teeth, and the spee and side curvatures of the row of teeth.

Namely, in the eccentric motion of the average movement articulator capable of being set for free movement or three-dimentional movement, the averaging joint and the joint for free movement cooperate in a complementary manner or the averaging joint controls the free movement, so that the average movement articulator is able to simulate the movement of the patient's jaws, and to perform average opening and closing motion and eccentric movement including the vertical, lateral longitudinal and swinging movement of the upper frame.

Even if the cuspal contact in an intercuspal position is incorrect when the upper and lower working casts are in centric occlusion, the upper and lower working casts can be brought into close cuspal contact in intercuspal position by the vertical movement of the upper frame. Accordingly, the height of a restored tooth will not be excessively large after correction. The capability of the upper frame in lateral movement enables movement similar to immediate side shift, i.e., slight lateral movement immediately before eccentric movement. The swing motion of the upper frame enables the correction of small errors in the working casts when the working casts are attached to the upper and lower frames in centric occlusion.

The movement of the upper frame toward the front causes the lower jaw to move backward after positioning the lower jaw in a habitual centric occlusion relative to the upper jaw, which enables the correction of clinical centric occlusion to approximate centric occlusion.

The average movement articulator functions for average movement when the upper frame and the transverse member are fastened together with the fastening means, such as screws, and the upper frame is turned and moved eccentrically on the transverse member.

DETAILED DESCRIPTION OF THE PREFERRED EMBODIMENT

Figure 1:
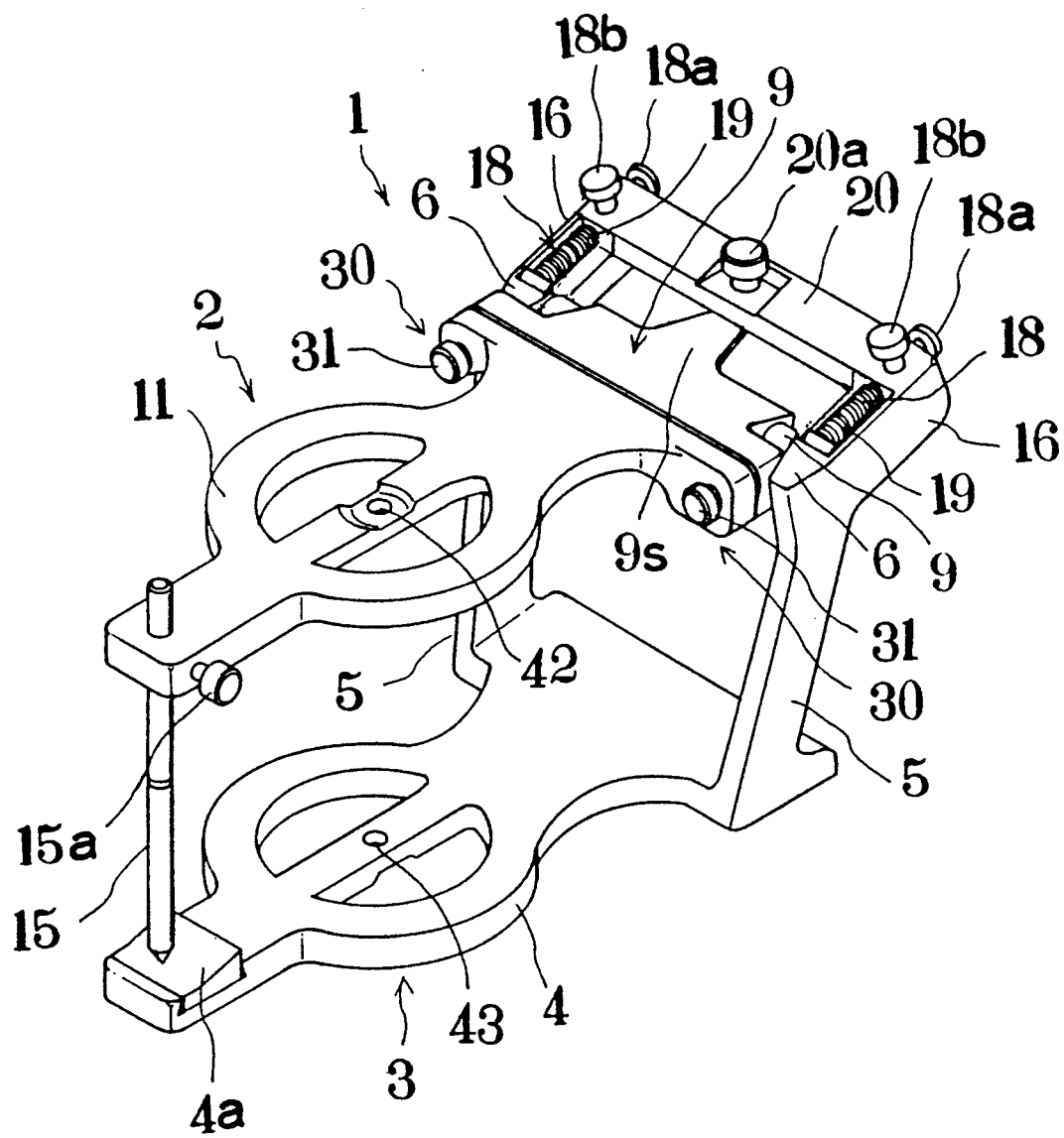
FIG. 1 is a perspective view of an average movement articulator capable of being set for free movement, in a preferred embodiment according to the present invention.
Figure 2:
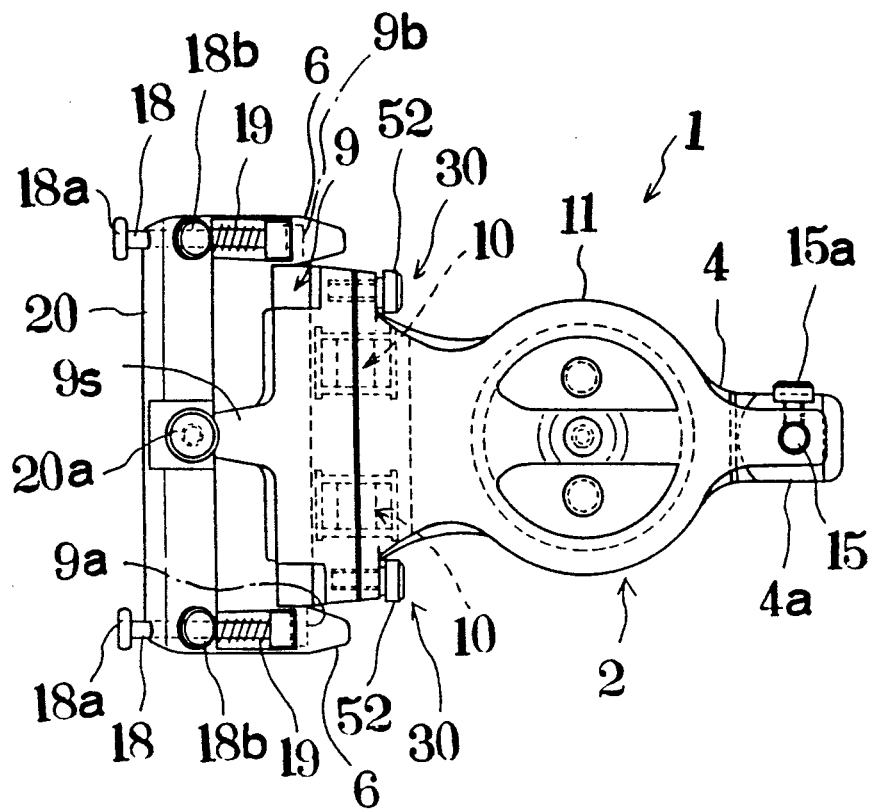
FIG. 2 is a plan view of the average movement articulator of FIG. 1.
Figure 3:
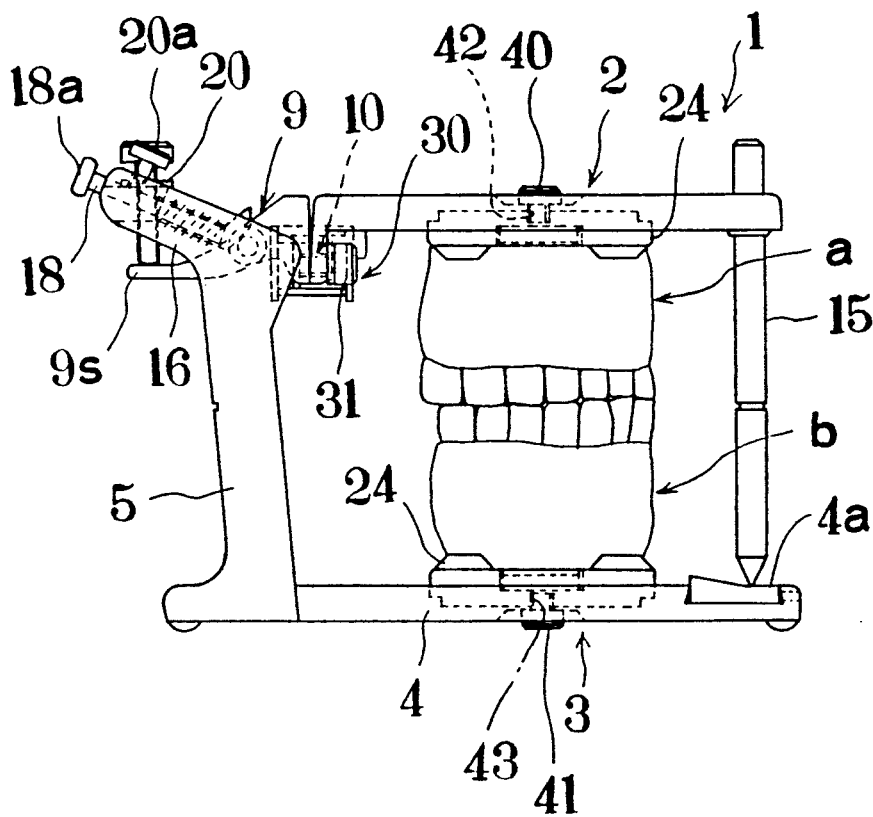
FIG. 3 is a side view of the average movement articulator of FIG. 1.
Figure 4:
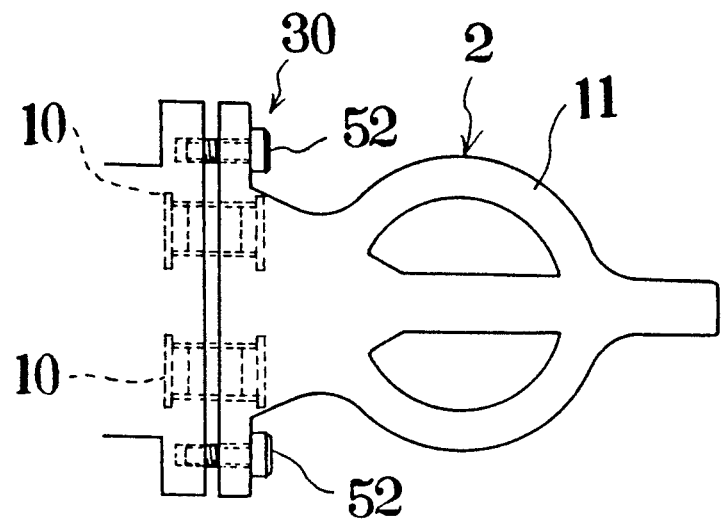
FIG. 4 is a view of assistance in explaining a mode of free movement in accordance with the present invention.
Figure 5:
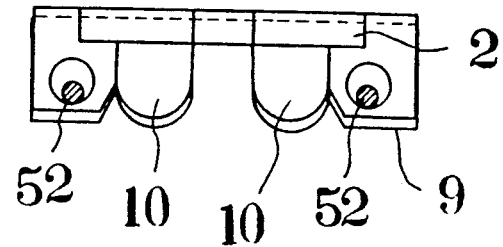
FIG. 5 is a view of assistance in explaining a mode of free movement in accordance with the present invention.

An average movement articulator in a preferred embodiment according to the present invention will be described hereinafter with reference to the accompanying drawings (FIGS. 1 to 5). FIG. 1 is a perspective view of the average movement articulator 1 of the present invention, FIG. 2 is a plan view of the average movement articulator of FIG. 1, FIG. 3 is a side view of the average movement articulator of FIG. 1, FIG. 4 is a front view of the average movement articulator of FIG. 1 and FIG. 5 is a rear view of an upper frame 2 and a transverse member 9 connected by resilient connecting members 10.

Referring to FIGS. 1 to 3, the average movement articulator 1 comprises, as a principal components, an upper frame 2 and a lower frame 3. An upper working cast 'a' and a lower working cast 'b' are attached, respectively, to the upper frame 2 and the lower frame 3. The upper working cast 'a' and the lower working cast 'b' are in occlusal relation. The occlusal condition of the upper working cast 'a' and the lower working cast 'b' is observed to determine measures for the restoration of a decayed tooth or the fabrication of a denture.

The construction of the upper frame 2 and the lower frame 3 will be described concretely with reference to FIGS. 1 to 3. The lower frame 3 has a substantially triangular base 4 and support struts 5 extending upright, respectively, from the opposite ends of the rear end of the base 4. The lower working cast 'b' is attached in the central area of the front portion of the base 4.

The upper frame 2 which is disposed above the lower frame 3, as described hereinafter, has the rear end thereof vertically pivotally connected to the upper portion of the left and right support struts 5 by way of a transverse member 9. As best shown in FIG. 2, holes 42 and 43 are formed in the upper frame 2 and the lower frame 3 to receive bolts 40 and 41 therethrough, respectively.

The support struts 5 are provided with recesses 6 to receive trunnions 9a and 9b formed at the opposite ends of the transverse member 9 with a sufficient degree of freedom, respectively, so that the transverse member 9 is able to move longitudinally and to swing about a lateral axis.

The rear end of the upper frame 2 is joined to the front end of the transverse member 9 by the resilient connecting members 10, such as springs which will be described later in details, in such a manner that the upper frame 2 is able to move longitudinally, vertically and laterally and to turn relative to the transverse member 9. The upper working cast 'a' is attached to the lower surface of a substantially circular base 11 formed in the upper frame 2.

The mode of movement of the upper frame 2 relative to the transverse member 9 will be described with reference to FIGS. 4 to 9.

The relative longitudinal movement of the upper frame 2 is the movement of the upper frame 2 along the longitudinal axis relative to the transverse member 9, compressing or extending the resilient connecting members 10 as shown in FIG. 4.

The relative vertical movement of the upper frame 2 is the vertical movement of the upper frame 2 relative to the transverse member 9 as shown in FIG. 5, compressing or extending the resilient connecting members 10.

Figure 6:
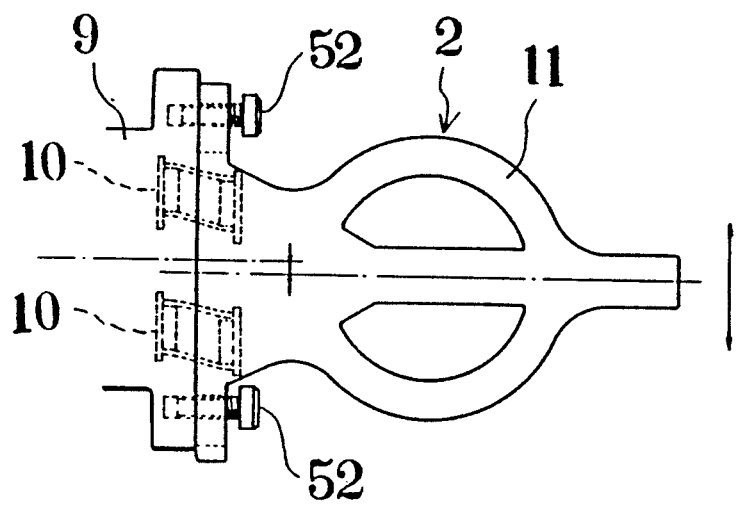
FIG. 6 is a view of assistance in explaining a mode of free movement in accordance with the present invention.

The relative lateral movement of the upper frame 2 is the lateral movement, namely, the movement along a lateral axis perpendicular to the longitudinal axis of the upper frame 2 relative to the transverse member 9 as shown in FIG. 6, compressing or extending the resilient connecting members 10.

Figure 7:
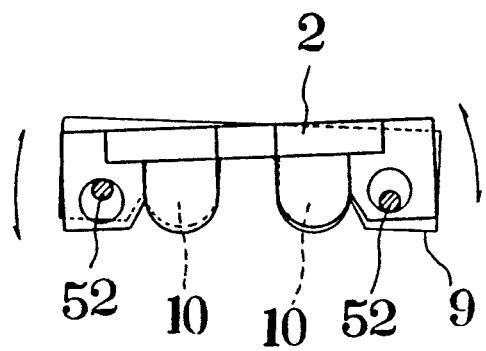
FIG. 7 is a view of assistance in explaining a mode of free movement in accordance with the present invention.
Figure 8:
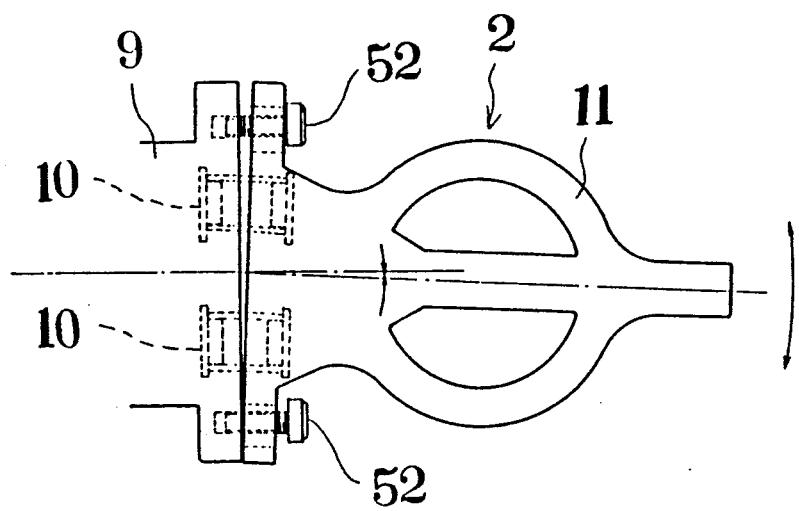
FIG. 8 is a view of assistance in explaining a mode of free movement in accordance with the present invention.
Figure 9:
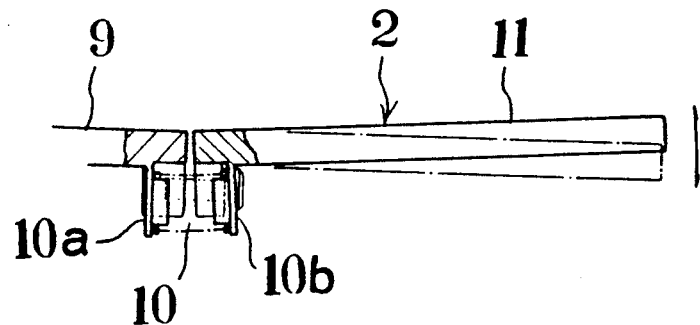
FIG. 9 is a view of assistance in explaining a mode of free movement in accordance with the present invention.

The relative turning movement of the upper frame 2 is the turning movement of the upper frame 2 about the longitudinal axis relative to the transverse member 9 as shown in FIG. 7, compressing or extending the resilient connecting members 10, the lateral displacement of the upper frame 2 from the longitudinal axis relative to the transverse member 9 as shown in FIG. 8, or the vertical displacement of the upper frame 2 from the longitudinal axis relative to the transverse member 9 as shown in FIG. 9.

The resilient connecting members 10 may connect the upper frame 2 and the transverse member 9 in any suitable manner. In this embodiment, as shown in FIGS. 10 and 11, holding plates 10a are attached to the lower surface of the transverse member 9 near the opposite ends of the front portion of the transverse member 9, holding plates 10b are attached to the lower surface of the upper frame 2 at positions near the rear end of the upper frame 2 and corresponding to the holding plates 10a, and the opposite ends of each resilient connecting member 10 are attached to the holding plates 10a and 10b, respectively.

Figure 10:
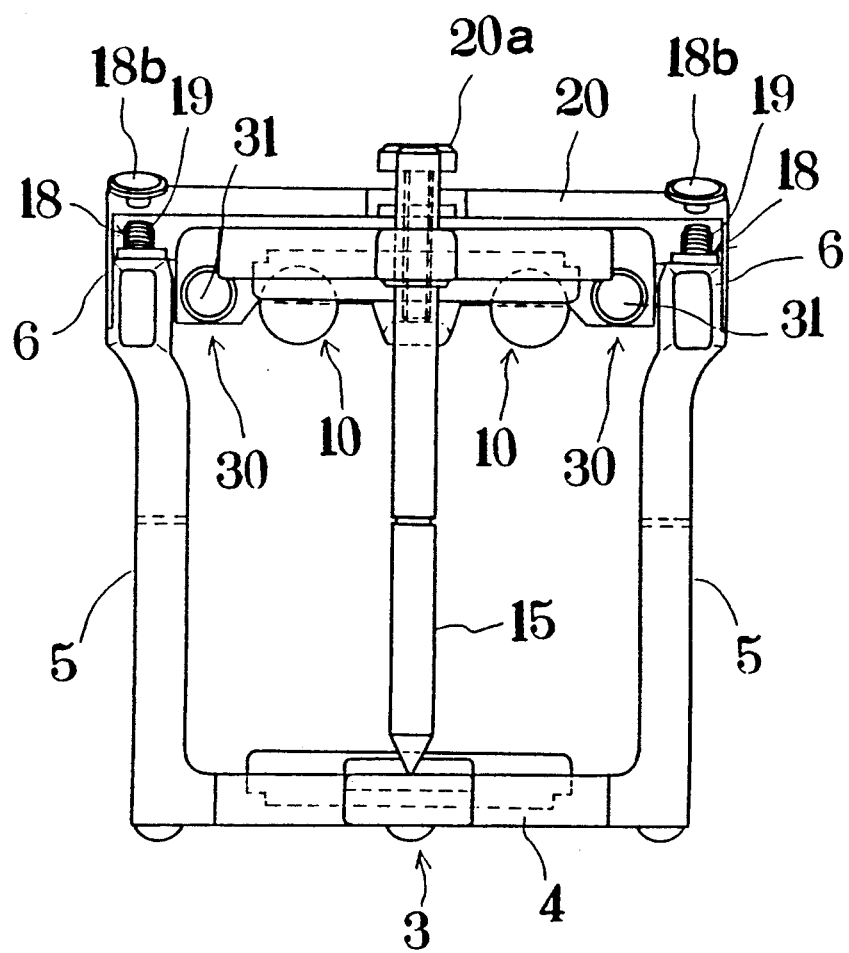
FIG. 10 is a front view of the average movement articulator of FIG. 1.
Figure 11:
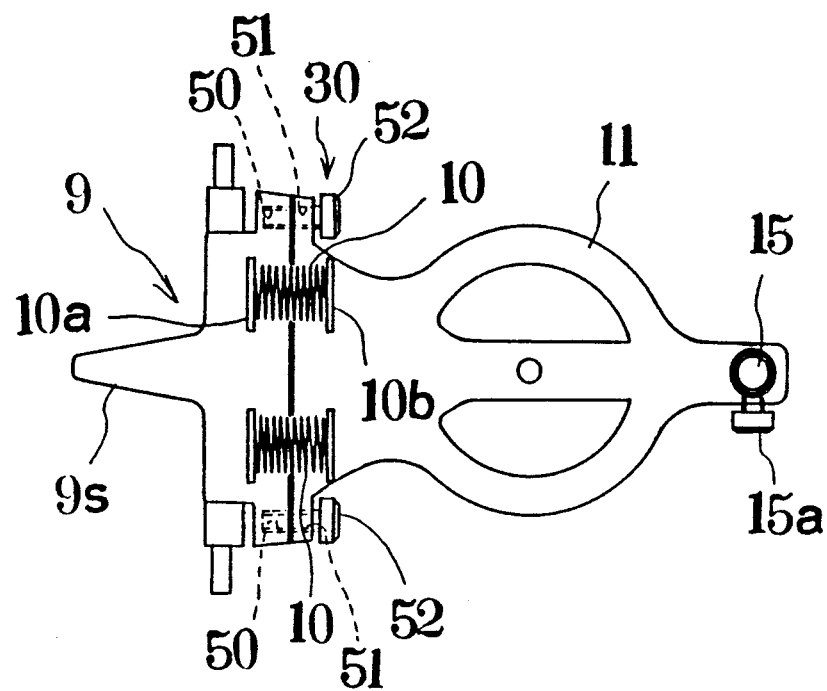
FIG. 11 is a bottom view of an upper frame included in the average movement articulator of FIG. 1.

As shown in FIGS. 10 and 11, the resilient connecting members 10 are not compressed and the rear end of the upper frame 2 is in contact with the front end of the transverse member 9 when the upper frame 2 is in the normal position relative to the transverse member 9. In this state, the upper frame 2 and the transverse member 9 move in a unit or synchronously for eccentric movement and opening and closing movement in a centric occlusal position. The upper frame 2 can readily be fastened to the transverse member 9 by fastening means 30.

In this embodiment, the resilient connecting members 10 are tension coil springs as best shown in FIG. 11. The resilient connecting members 10 may be formed of an elastic or resilient material, such as rubber.

In FIG. 10 and FIG. 11, numeral 30 indicates a fastening means which fastens the upper frame 2 firmly to the transverse member 9 to use the upper frame 2 as a member of an ordinary average movement articulator.

The fastening means 30 comprises bolts 52 inserted in through holes 51 formed in the upper frame 2 at positions outside the resilient connecting members 10, and screwed in threaded holes 50 formed in the transverse member 9 at positions outside the resilient connecting members 10 and corresponding to the through holes 51.

As shown in FIG. 1 to FIG. 3, an incisal pin 15 which can adjust the length thereof is vertically disposed on the front end portion of an upper frame plate 11. The lower end of the incisal pin 15 is made come into contact with an incisal table 4a mounted on the front extremity of the lower frame mounting base 4 so that the upper frame 2 is supported at a desired height while defining a desired space between the upper frame 2 and the lower frame 3 thus assuring an occlusal position and the incisal guidance is formed. In the drawings, 15a indicates a height adjustable bolt mounted on the front extremity of the upper frame plate 11.

As shown in FIGS. 1 and 3, the upper end of the support struts 5 are extended obliquely upward toward to rear to form inclined support arms 16. The trunnions 9a and 9b of the transverse member 9 received in the recesses 6 are able to slide along the inclined upper surfaces of the inclined support arms 16. The inclined support arms 16 and the trunnions 9a and 9b are the components of an averaging joint of the average movement articulator 1.

The inclined upper surfaces of the inclined support arms 16 are inclined at an angle of 23° in an average to a horizontal plane to determine an inclination of sagittal condyle path. The inclination of sagittal condyle path, however, can optionally be determined taking into consideration the size and shape of the patient's jaws or the average mevement articulator 1.

When eccentrically moving the working casts 'a' and 'b' attached, respectively, to the upper frame 2 and the lower frame 3 in either a free movement mode or an average movement mode, the transverse member 9 slides along the inclined surfaces of the inclined support arms 16 having the inclination of sagittal condyle path to guide the upper frame 2 along the sagittal condyle path.

Figure 12:
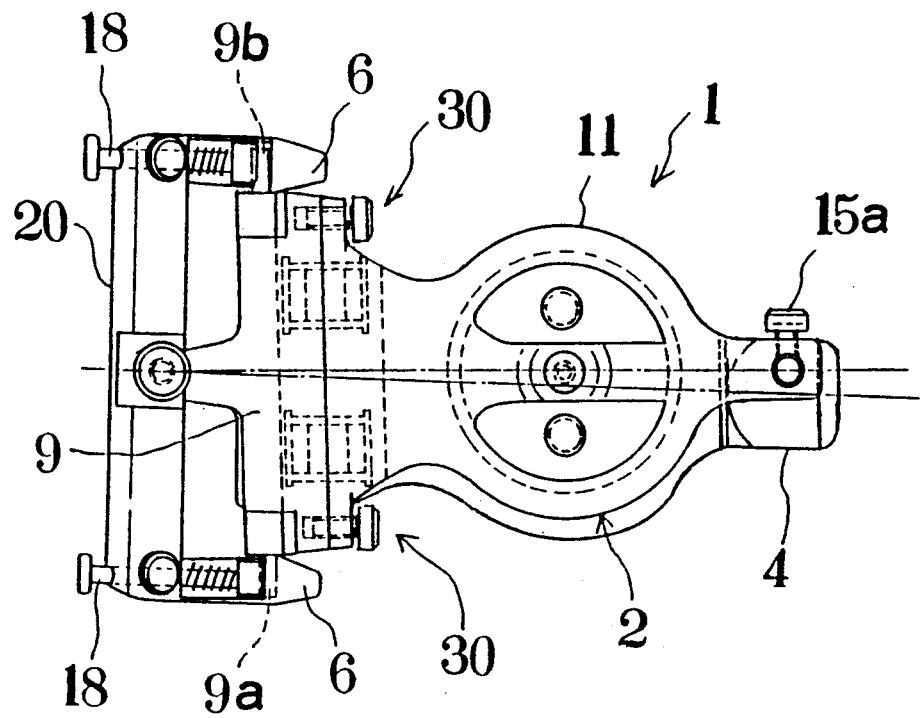
FIG. 12 is a view of assistance in explaining the positional relation between the upper frame and a transverse member included in the average movement articulator of FIG. 1.

When moving the upper frame 2 along the sagittal condyle path, as shown in FIG. 12, the transverse member 9 can be turned on the trunnion 9a in a plane including the transverse member 9 together with the upper frame 2.

When the fastening means 30 are loosened to enable the upper frame 2 to move relative to the transverse member 9 to set the average movement articulator 1 for free movement, an occlusal state substantially equivalent to actual occlusal state can be realized by allowing the transverse member 9 to move for eccentric movement, and opening and closing in the centric occlusal position according to the abraded surfaces of the patient's teeth, the height of the cusps, the positions of the patient's teeth and the spee and side curvatures of the row of the patient's teeth.

Either when the fastening means 30 is loosened to set the average movement articulator for free movement or when the fastening means 30 is tightened to set the average movement articulator 1 for average movement, the transverse plate 9 and the upper frame 2 are turned with the trunnions 9a and 9b of the transverse plate 9 seated firmly in the recesses 6.

Presser rods 18 are extended along the upper surfaces of the inclined support arms 16 and coil springs 19 are put on the presser rods 18 respectively to make the presser rods 18 press the trunnions 9a and 9b of the transverse member 9 resiliently. The presser rods 18 are provided with knobs 18a by which the presser rods 18 are moved to remove pressure applied to the trunnions 9a and 9b.

Thus, the presser rods 18 holds the trunnions 9a and 9b in the recesses 6 and enables the transverse member 9 to turn smoothly on the trunnions 9a and 9b. When removing the transverse member 9 from the inclined support arms 16, the knobs 18a are pulled and the trunnions 9a and 9b of the transverse member 9 are removed from the recesses 6. Indicated at 18b are stop screws for fastening the presser rods 18.

A cross frame 20 is extended between the inclined support arms 16, which are components of the averaging joint of the average movement articulator 1, and an adjusting screw 20a is provided on the cross frame 20 so that the lower extremity of the adjusting screw 20a is contact with a lug 9s extending to the rear from the rear end of the transverse member 9. The height of the upper frame 2 is adjusted by turning the adjusting 29a. When an incisal pin 15 is removed to secure the visibility of the front portion of the average movement articulator 1, the upper frame 2 is held in place by the adjusting screw 20a instead of the incisal pin 15 to maintain the occlusal position of the upper working cast 'a' and the lower working cast 'b'.

As shown in FIG. 3, the upper working cast 'a' and the lower working cast 'b' are mounted, respectively, on mounting plates 24 and the mounting plates 24 holding the upper working cast 'a' and the lower working cast 'b' are fastened to the upper frame 2 and the lower frame 3 with the screws 40 and 41 and plaster, respectively. The upper working cast 'a' and the lower working cast 'b' may be joined directly to the upper frame 2 and the lower frame 3 with plaster.

As shown in FIG. 3, the mounting plates 24 are provided with magnets to facilitate the mounting of the upper working cast 'a' and the lower working cast 'b' on and removing the same from the upper frame 2 and the lower frame 3.

Figure 13:
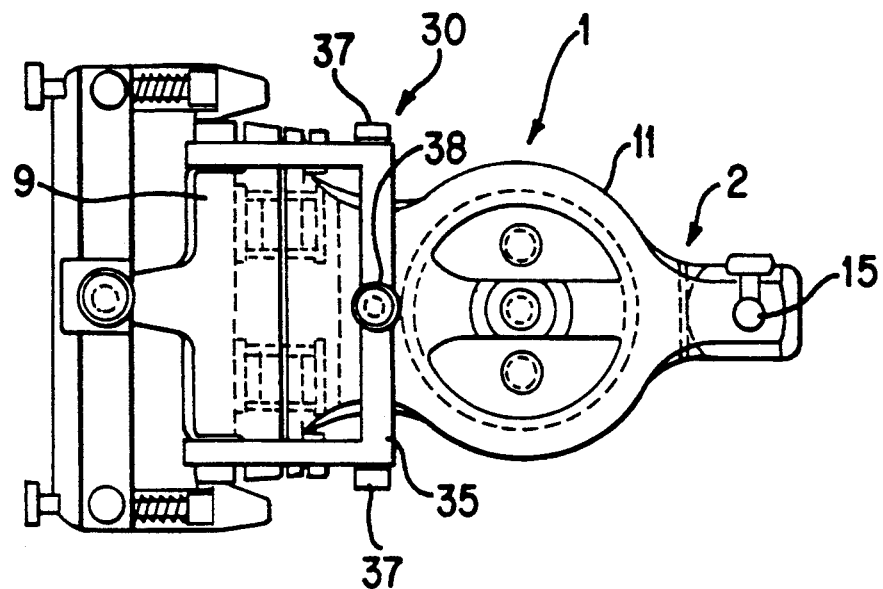
FIG. 13 is a plan view of a modification of the average movement articulator of FIG. 1.
Figure 14:
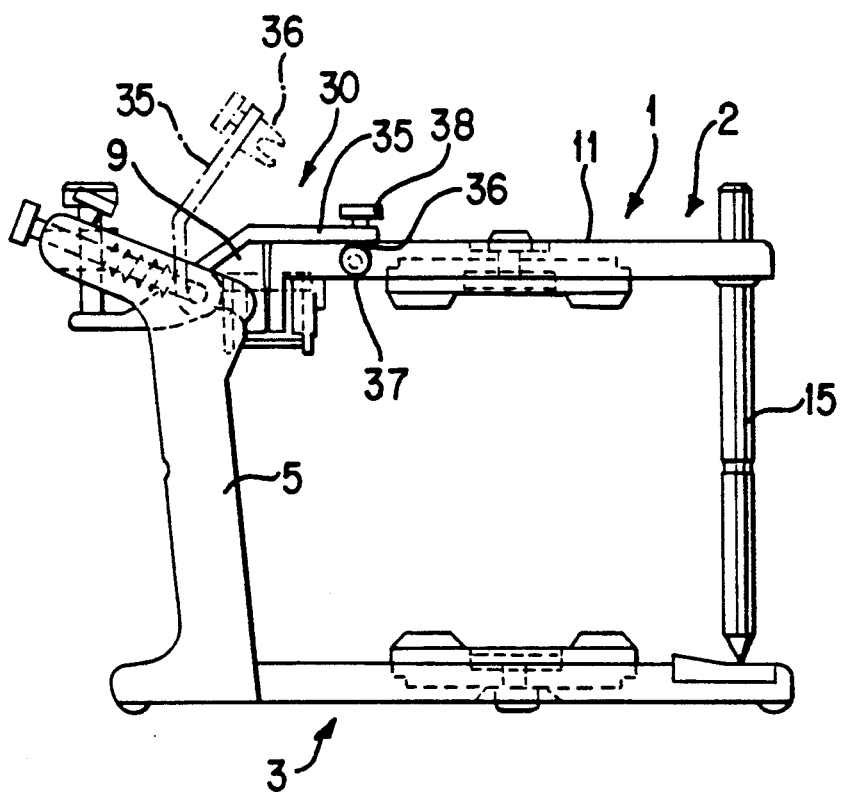
FIG. 14 is a side view of the average movement articulator of FIG. 13.

FIGS. 13 and 14 show fastening means 30 in a modification. This fastening means 30 comprises an upper frame fastening member 35 pivotally supported on the transverse member 9 and provided with bifurcated projection 36 at the opposite ends of a front portion thereof, and screws 37 meshed, respectively, in the opposite side surfaces of the base 11 of the upper frame 2. When fixing the upper frame 2 to the transverse member 9, the bifurcated projections 36 are brought into engagement with the screws 37.

Thus, the transverse member 9 and the base 11 of the upper frame 2 are fastened together in a single unit to use the average movement articulator 1 as an ordinary average movement articulator.

A screw 38 provided at the middle of the front end of the frame fastening member 35 is screwed in a threaded hole formed in the base 11 of the upper frame to fasten the frame fastening member 35 to the base 11 of the upper frame 2.

A method of using the average movement articulator 1 capable of being set for free movement thus constructed will be described hereinafter.

When the fastening means 30 is loosened to set the average movement articulator 1 for free movement, the average movement articulator 1 has a second joint having the resilient connecting member 10 allowing the free movement of the upper frame 2 relative to the transverse member 9, in addition to the joint joining the transverse member 9 holding the upper frame 2 to the inclined support arms 16.

Accordingly, the upper frame 2 is able to move vertically, laterally and longitudinally and to turn or swing on the joints of the average movement articulator 1 for eccentric movement to enable the upper working cast 'a' held on the upper frame 2 move according to the movement of the patient's jaws, i.e., according to the abraded surface of the patient's teeth, the height of the cusps, the positions of the patient's teeth and the spee and side curvatures of the row of the patient's teeth.

Since the movement of the averaging joint and that of the joint for free movement complement each other, the upper frame 2 is able to perform eccentric movement smoothly according to the movement of the patient's jaws. The free movement of the upper frame 2 includes the vertical mevement, the lateral movement, the turning motion and the longitudinal movement.

The vertical movement of the upper frame 2 of the average movement articulator 1 enables close occlusion of the working casts 'a' and 'b' in an intercuspal position even if the intercuspal position in the centric occlusion is incorrect. Therefore, the restored tooth exhibits poor occlusion after correction. The capability of the upper frame 2 in lateral movement enables movement similar to immediate side shift, i.e., slight lateral movement immediately before eccentric movement. The swing motion of the upper frame 2 enables the correction of slight errors in the occlusion of the upper working cast 'a' and the lower working cast 'b' in the centric occlusion.

The movement of the upper frame 2 toward the front causes the lower jaw to move backward after positioning the lower jaw in a habitual centric occlusion relative to the upper jaw, which enables the correction of clinical centric occlusion to approximate centric occlusion.

The average movement articulator 1 functions for average movement when the upper frame 2 and the transverse member 9 are fastened together with the fastening means 30, and the upper frame 2 is turned for operation as a general average movement articulator.

While the present invention has been described in its preferred embodiment, the present invention is not limited thereto in its practical application and many modifications are possible without derarting from the scope of the present invention. For example, the support struts 5 may be substituted by a single flat support plate.

I claim:

1. An average movement articulator capable of being set for free movement, comprising:
    a) a lower frame holding a lower working cast on its upper surface;
    b) an upper frame disposed above the lower frame and holding an upper working cast on its lower surface;
    c) a pair of support struts standing upright at the opposite ends, respectively, of the rear end of the lower frame;
    d) a transverse member supported on the respective upper ends of the support struts so as to be swingable about a lateral axis and longitudinally movable; and
    e) resilient connecting members resiliently connecting the rear end of the upper frame to the transverse member so that the upper frame is able to move vertically, laterally and longitudinally and to turn relative to the transverse member;
    f) wherein the upper frame is able to move longitudinally, vertically and laterally and to swing about a lateral axis relative to the lower frame.

2. The average movement articulator capable of being set for free movement according to claim 1, wherein inclined support arms extend obliquely upward toward the rear from the upper ends of the support struts, respectively, the transverse member is movable along the upper surfaces of the support arms, the transverse member is pressed resiliently against the inclined support arms by presser rods, the upper frame is able to move longitudinally together with the transverse member along the inclined surfaces of the inclined support arms, and the upper frame is able to swing about a lateral axis.

3. The average movement articulator capable of being set for free movement according to claim 1, wherein the upper frame is provided with fastening means for fastening together the upper frame and the transverse member.

* * * * *